United States Patent
Zhu et al.

(10) Patent No.: US 9,063,186 B2
(45) Date of Patent: Jun. 23, 2015

(54) DEVICE FOR MEASURING ELECTRICAL TREEING OF MEDIUM VOLTAGE CABLES

(71) Applicants: Tianjin Electric Power Corporation, Tianjin (CN); State Grid Corporation of China, Beijing (CN)

(72) Inventors: Xiaohui Zhu, Tianjin (CN); Zhengzheng Meng, Tianjin (CN); Fengzheng Zhou, Tianjin (CN)

(73) Assignees: TIANJIN ELECTRIC POWER CORPORATION, Tianjin (CN); STATE GRID CORPORATION OF CHINA, Beijing (CN)

( * ) Notice: Subject to any disclaimer, the term of this patent is extended or adjusted under 35 U.S.C. 154(b) by 86 days.

(21) Appl. No.: 14/077,189

(22) Filed: Nov. 11, 2013

(65) Prior Publication Data
US 2014/0070818 A1    Mar. 13, 2014

Related U.S. Application Data

(63) Continuation-in-part of application No. PCT/CN2012/074600, filed on Apr. 24, 2012.

(51) Int. Cl.
*G01R 31/02* (2006.01)
*H01B 7/28* (2006.01)
*G01N 27/20* (2006.01)
*G01R 31/12* (2006.01)

(52) U.S. Cl.
CPC ............ *G01R 31/021* (2013.01); *G01R 31/025* (2013.01); *G01R 31/1272* (2013.01); *H01B 7/2813* (2013.01); *G01N 27/205* (2013.01)

(58) Field of Classification Search
CPC ............ G01R 31/1272; G01R 31/021; G01R 31/022; G01R 31/083; G01R 31/025; G01R 31/08; G01R 27/18
USPC .......... 324/541, 509, 544, 551–556; 340/647, 340/651
See application file for complete search history.

(56) References Cited

U.S. PATENT DOCUMENTS 3,821,640 A * 6/1974 Bahder et al. ................ 324/544
5,469,066 A * 11/1995 Ito et al. ...................... 324/551
(Continued)

FOREIGN PATENT DOCUMENTS

CN          102890226 A  *  1/2013  ............ G01R 31/12

OTHER PUBLICATIONS

Al-Arainy et al., The Performance of Strippable and Bonded Screened Medium-Voltage XLPE-Insulated Cables Under Long-Term Accelerated Aging, Apr. 2007, IEEE Transactions on Power Delivery, vol. 22, 1-8.*

(Continued)

*Primary Examiner* — Patrick Assouad
*Assistant Examiner* — Sean Curtis
(74) *Attorney, Agent, or Firm* — Matthias Scholl P.C.; Matthias Scholl

(57) ABSTRACT

A device for measuring electrical treeing of medium voltage cables. The device includes a plurality of test units connected in parallel. Each test unit includes: a test cup and an insulating base. The test cup includes an inner cavity for accommodating a salt solution, an insulating cover equipped with a first electrode, and an opening. The insulating base includes a side wall, an insulating washer, a second electrode, a conductor, and a through hole from top to bottom. The test cup is disposed on the insulating base. The lower part of the test cup is surrounded by the side wall and presses on the upper surface of the insulating washer. The lower part of the test cup is in threaded connection with the side wall. The space between the opening and the test sample is sealed by the insulating washer.

3 Claims, 3 Drawing Sheets

(56) References Cited

U.S. PATENT DOCUMENTS

| | | | |
|---|---|---|---|
| 6,617,859 B1 * | 9/2003 | Orton | 324/544 |
| 6,621,276 B2 * | 9/2003 | Wen et al. | 324/541 |
| 7,615,247 B2 * | 11/2009 | Bertini et al. | 427/117 |
| 8,205,326 B2 * | 6/2012 | Bertini et al. | 29/828 |
| 8,656,586 B2 * | 2/2014 | Bertini et al. | 29/857 |
| 2014/0055149 A1 * | 2/2014 | Zhu et al. | 324/693 |
| 2014/0070818 A1 * | 3/2014 | Zhu et al. | 324/541 |

OTHER PUBLICATIONS

Bao et al., The Initiation Phenomena of Electrical Treeing in XLPE Cable Insulation, Sep. 17-20, 2012, 2012 International Conference on High Voltage Engineering and Application, 1-4.*

Ying et al., A Novel Method for the Insulation Thickness Design of HV XLPE Cable Based on Electrical Treeing Tests, Xi'an Jiaotong University, Feb. 2014, 1-7.*

Thiamsri et al., Effect of Applied Voltage Frequency on Electrical Treeing in 22kV Cross-linked Polyethylene Insulated Cable, Dec. 28, 2011, World Academy of Science, Engineering, & Technology, 1-6.*

Johansson et al., Detection of Electrical Treeing in XLPE Exposed to AC and DC stress, 2010, Chalmers University of Technology, Section 4-5 (see pp. v-vi).*

Vogelsang et al., Detection of Electrical Tree Propagation by Partial Discharge Measurments, 2002, $15^{th}$ International Conference on Electrical Machines, ICEM 2002, 1-6.*

* cited by examiner

DEVICE FOR MEASURING ELECTRICAL TREEING OF MEDIUM VOLTAGE CABLES

CROSS-REFERENCE TO RELATED APPLICATIONS

This application is a continuation-in-part of International Patent Application No. PCT/CN2012/074600 with an international filing date of Apr. 24, 2012, designating the United States, now pending, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

1. Field of the Invention

The invention relates to the field for measuring power cables, and more particularly to a device for measuring electrical treeing in XLPE medium voltage cables.

2. Description of the Related Art

Crosslinked polyethylene (XLPE) medium voltage power cables are widely used because of convenient maintenance. However, electrical treeing in the cable insulation is always a main factor that affects the safety and stability of the cables.

Electrical treeing resistant XLPE (TR-XLPE) medium voltage power cable is a new kind of power cable that is able to prolong the service life of the XLPE cables. The production cost of the TR-XLPE medium voltage power cable is approximately 10%-20% higher than that of the common XLPE medium voltage power cable. However, these two kinds of cables have no difference in appearance, and thus, an electrical treeing experiment is required for measuring the electrical treeing resistance.

A typical method for measuring electrical treeing resistance of XLPE medium voltage power cables includes: using heat treated cables as test samples, placing each cable inside a polyethylene tube or a polyvinyl chloride tube having an inner diameter of 75 mm, and applying a test voltage to facilitate the electrical treeing. During the electrical treeing test, water is injected into the interspace of conductors of the test samples and the tubes. The test samples are required to be heated by inductive current for load cycles, and then examine and count the electrical treeing after the test.

The method has the following disadvantages:

1) the method can only take cable core of finished power cable as test sample; the test device has a large volume and the operation for the test is complicate and cumbersome; and 2) the test period for electrical treeing is long; performing the electrical treeing test on the test samples is time consuming, so that the method cannot fast evaluate whether the cable materials have the property of electrical treeing resistance.

SUMMARY OF THE INVENTION

In view of the above-described problems, it is one objective of the invention to provide a device for measuring electrical treeing of medium voltage cables that has a small volume and short period for measuring electrical treeing, and is capable of fast evaluating the electrical treeing property.

To achieve the above objective, in accordance with one embodiment of the invention, there is provided a device for measuring electrical treeing of medium voltage cables comprising a plurality of test units connected in parallel. Each test unit comprises: a test cup, the test cup comprising an inner cavity for accommodating a salt solution, an insulating cover equipped with a first electrode, and an opening; and an insulating base, the insulating base comprising a side wall, an insulating washer, a second electrode, a conductor, and a through hole from top to bottom. The test cup is disposed on the insulating base. The insulating cover is disposed on the test cup. A lower end of the first electrode is immersed into the salt solution; and the opening is formed on a bottom of the test cup. The through hole is arranged on a center of the insulating base; an upper part of the through hole has a larger diameter than a lower part thereof so as to form a recess. The second electrode is received by the recess, and an upper surface of the second electrode is at the same level as an upper surface of the insulating base. A test sample is applied to the second electrode. A diameter of the insulating washer is larger than that of the opening arranged on the bottom of the test cup and is smaller than that of the second electrode. The conductor is connected to the second electrode and is grounded. An edge of the insulating base extends upwards to form the side wall. A lower part of the test cup is surrounded by the side wall and presses on an upper surface of the insulating washer. The lower part of the test cup is in threaded connection with the side wall, and a space between the opening and the test sample is sealed by the insulating washer.

In a class of this embodiment, the test sample is selected from an insulating layer of an XLPE medium voltage cable, and a thickness thereof is 1 mm.

In a class of this embodiment, the plurality of the test units are arranged inside a test box; a bottom of the test box is grounded; the insulating base of each test unit is fixed inside the test box; and each of the second electrodes is connected to the bottom of the test box via a corresponding conductor.

Advantages of the invention are summarized as follows:

1. The device of the invention has a simple structure, small volume, and convenient operation, and is capable of directly using insulating layers of XLPE and TR-XLPE cables to measure electrical treeing.

2. Period for the electrical treeing measurement is short. Under the test voltage, electrical treeing test is performed on the test samples for some time, such as one day, five days, and ten days, followed by physical and chemical properties and electric performance tests on the deteriorated XLPE and TR-XLPE test samples so that TR-XLPE cables and common XLPE cables can be fast classified according to relative parameters of the physical and chemical properties and the electric performance test. The device of the invention largely shortens the period for testing, and achieves fast measurement of the electrical treeing property of the cable materials, thereby improving the working efficiency.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing a device for measuring electrical treeing of medium voltage cables are described below. It should be noted that the following examples are intended to describe and not to limit the invention.

Figure 3:
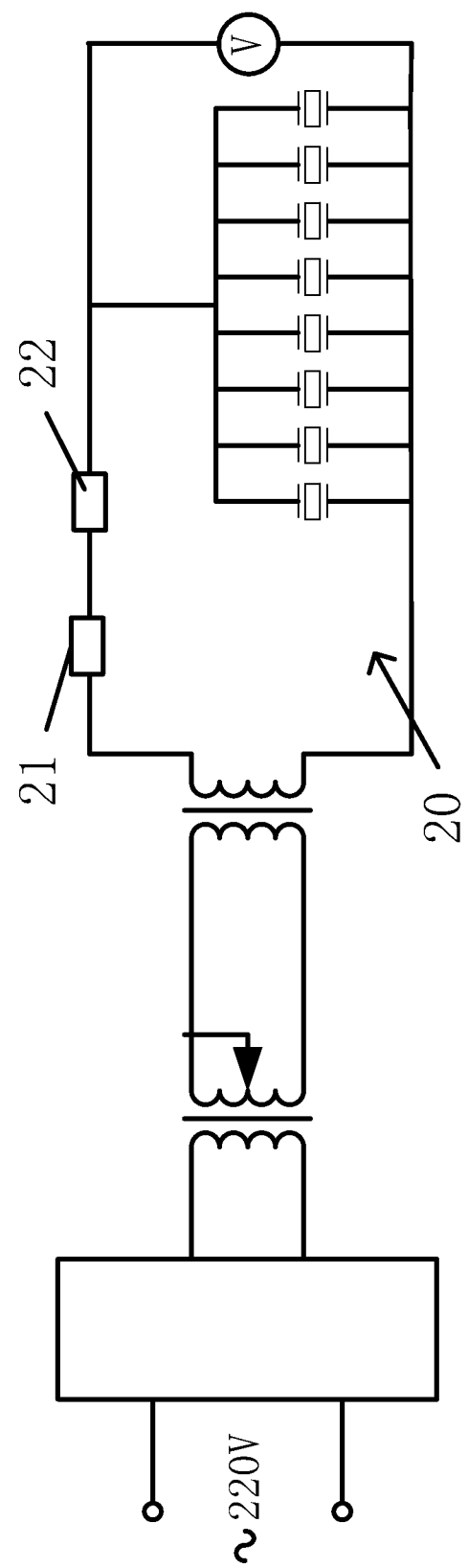
FIG. 3 is a circuit diagram of a device for measuring electrical treeing of medium voltage cables in accordance with one embodiment of the invention.

As shown in FIG. 3, a device for measuring electrical treeing of medium voltage cables comprises eight test units in parallel. The eight the test units are arranged inside a test box 13. The bottom of the test box 13 is grounded. The insulating base 2 of each test unit is fixed inside the test box 13; and each second electrode 8 is connected to the bottom of the test box 13 via a corresponding conductor 9. The number of the test units can be adjusted as needed. When a small number of the test samples are provided, the test can be directly carried out by the test unit.

Figure 1:
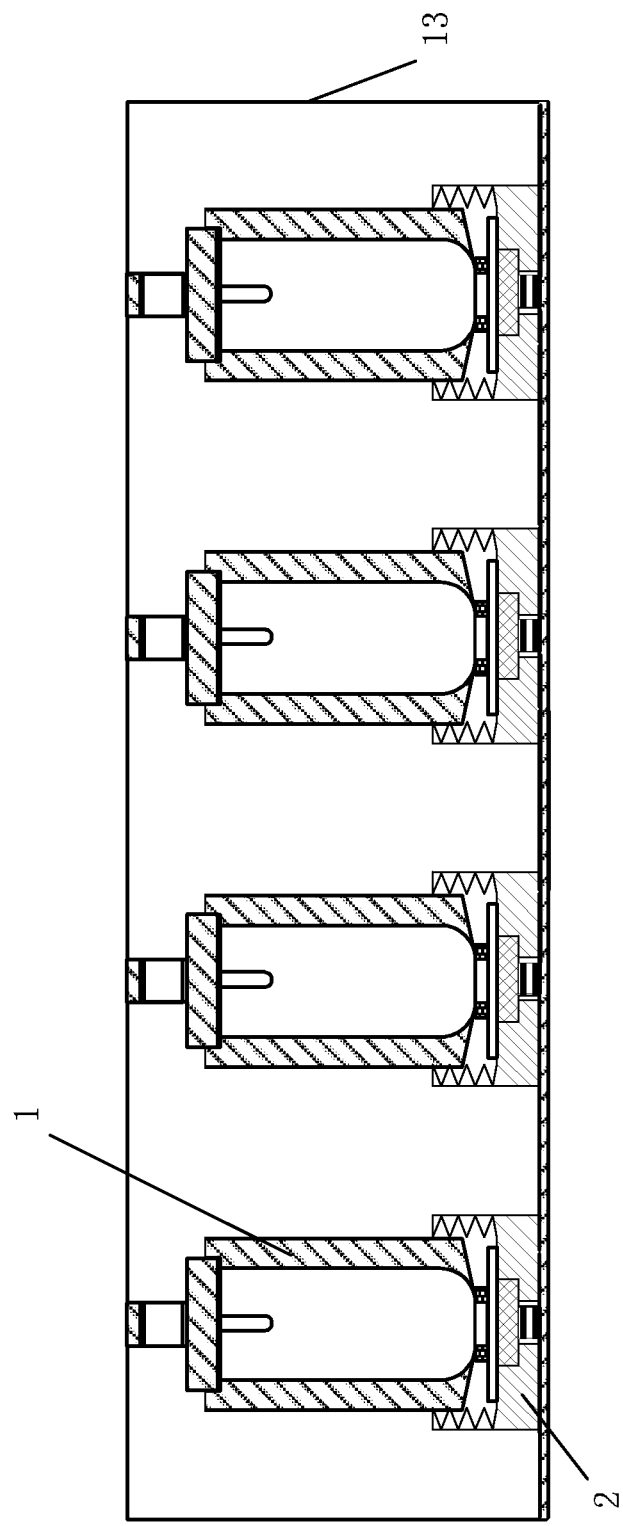
FIG. 1 is an assembly diagram of a device for measuring electrical treeing of medium voltage cables in accordance with one embodiment of the invention.
Figure 2:
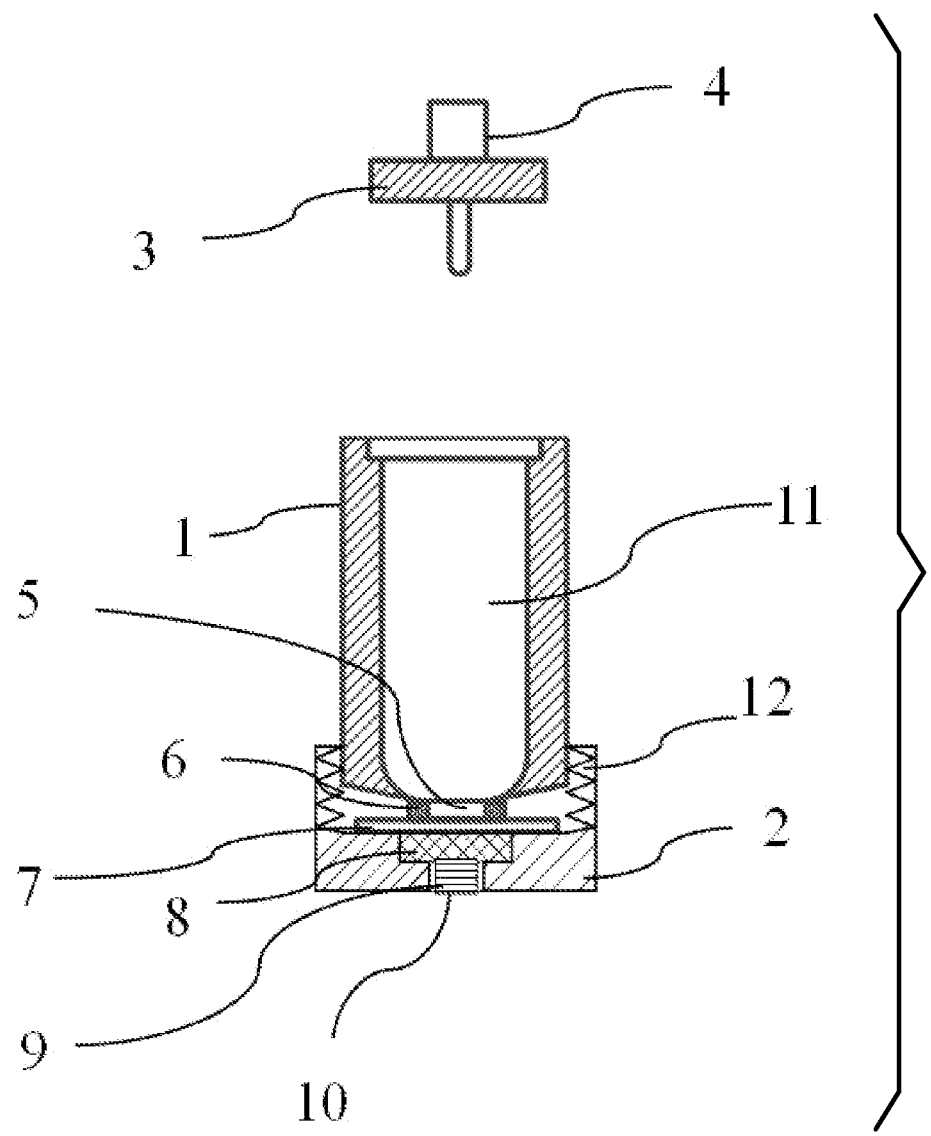
FIG. 2 is a structure diagram of a test unit of a device for measuring electrical treeing of medium voltage cables in accordance with one embodiment of the invention.

The structure of the test unit is shown in FIGS. 1 and 2. Each test unit comprises: a test cup 1, the test cup 1 comprising an inner cavity for accommodating a salt solution, an insulating cover 3 equipped with a first electrode 4, and an opening 5; and an insulating base 2, the insulating base 2 comprising a side wall 12, an insulating washer 6, a second electrode 8, a conductor 9, and a through hole 10 from top to bottom. The test cup 1 is disposed on the insulating base 2. The insulating cover 3 is disposed on the test cup 1. A lower end of the first electrode 4 is immersed into the salt solution; and the opening 5 is formed on a bottom of the test cup 1. The through hole 10 is arranged on a center of the insulating base 10; an upper part of the through hole 10 has a larger diameter than a lower part thereof so as to form a recess. The second electrode 8 is received by the recess, and an upper surface of the second electrode 8 is at the same level with an upper surface of the insulating base 2. A test sample 7 is applied to the second electrode 8. A diameter of the insulating washer 6 is larger than that of the opening 5 arranged on the bottom of the test cup 1 and is smaller than that of the second electrode 8. The conductor 9 is connected to the second electrode 8 and is grounded. An edge of the insulating base 2 extends upwards to form the side wall 12. A lower part of the test cup 1 is surrounded by the side wall 12 and presses on an upper surface of the insulating washer 6. The lower part of the test cup 1 is in threaded connection with the side wall 12, and a space between the opening 5 and the test sample 7 is sealed by the insulating washer 6.

The salt solution is a NaCl solution having a concentration of 9 g/L. The test sample 7 is an insulating layer of an XLPE or TR-XLPE medium voltage cable, and a thickness thereof is 1 mm. 10,000 V voltage is applied to two ends of each first electrode 4. The thickness of the test sample and the voltage value are controlled according to a breakdown field strength of the XLPE medium voltage cable.

Working instruction of the device of the invention are described herein combined with the circuit diagram of FIG. 3:

1) Place the test sample between the insulating washer and the insulating base to allow the upper surface and the lower surface of the test sample to contact with the lower surface of the insulating washer and the upper surface of the second electrode, respectively, and allow the upper surface of the insulating washer to contact with an edge of the opening arranged at the bottom of the test cup so that an opening of the insulating washer is disposed right beneath the opening of the bottom of the test cup. Screw the test cup to prevent the salt solution from leaking out of the test cup.

2) Place a plurality of test units respectively into the test box (the insulating bases are not in fixed connection with the bottom of the test box). The upper surface of the second electrode contacts with the lower surface of the test sample; the lower surface of the second electrode contacts with an upper end of the conductor arranged in the lower part of the insulating base, and a lower end of the conductor contacts with an upper surface of an electrode of the test box which is grounded.

3) Add the salt solution to the inner cavity of the test cup. The amount of the salt solution is controlled to allow the first electrode to be immersed therein. The salt solution contacts with the test sample via the opening arranged on the bottom of the test cup, and is prevented from leaking because of the sealing of the insulating washer.

4) Dispose the insulating cover on the test cup, connect the first electrode of each test unit to a power supply circuit 20 comprising an overcurrent protection device 21, a timer 22, and a voltmeter.

5) Connect the circuit, and apply 10,000 V voltage to the first electrode so that the electrical treeing of the test samples is accelerated under the action of the high voltage and the salt solution.

6) After the electrical treeing test lasts for a certain period, perform physical and chemical properties and electric performance tests on the XLPE and TR-XLPE test samples so as to fast classify TR-XLPE cables and common XLPE cables in accordance with relative parameters of the physical, chemical, and dielectric properties.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A device for measuring electrical treeing of cables, the device comprising a plurality of test units connected in parallel, and each test unit comprising:
   a) a test cup, the test cup comprising an inner cavity for accommodating a salt solution, an insulating cover equipped with a first electrode, and an opening; and
   b) an insulating base, the insulating base comprising a side wall, an insulating washer, a second electrode, a conductor, and a through hole from top to bottom;

wherein
   the test cup is disposed on the insulating base;
   the insulating cover is disposed on the test cup; a lower end of the first electrode is immersed into the salt solution; and the opening is formed on a bottom of the test cup;
   the through hole is arranged on a center of the insulating base; an upper part of the through hole has a larger diameter than a lower part thereof so as to form a recess; the second electrode is received by the recess, and an upper surface of the second electrode is at the same level as an upper surface of the insulating base; a test sample is applied to the second electrode; a diameter of the insulating washer is larger than that of the opening arranged on the bottom of the test cup and is smaller than that of the second electrode; the conductor is connected to the second electrode and is grounded; and
   an edge of the insulating base extends upwards to form the side wall; a lower part of the test cup is surrounded by the side wall and presses on an upper surface of the insulating washer; the lower part of the test cup is in threaded connection with the side wall, and a space between the opening and the test sample is sealed by the insulating washer.

2. The device of claim 1, wherein the test sample is selected from an insulating layer of an XLPE medium voltage cable, and a thickness thereof is 1 mm.

3. The device of claim 1, wherein
a plurality of the test units are arranged inside a test box;
a bottom of the test box is grounded;
the insulating base of each test unit is fixed inside the test box; and
each of the second electrodes is connected to the bottom of the test box via a corresponding conductor.

\* \* \* \* \*